United States Patent [19]
Latina et al.

[11] Patent Number: 5,174,304
[45] Date of Patent: Dec. 29, 1992

[54] ELECTROCYCLOABLATION APPARATUS AND METHOD

[76] Inventors: Mark A. Latina, 71 Paddock La., No. Andover, Mass. 01845; Robert I. Park, 13261 Droxford, Cerritos, Calif. 90701

[21] Appl. No.: 699,157

[22] Filed: May 13, 1991

Related U.S. Application Data

[63] Continuation-in-part of Ser. No. 480,742, Feb. 16, 1990, Pat. No. 5,025,811.

[51] Int. Cl.⁵ ............................................. A61N 1/30
[52] U.S. Cl. ..................................... 128/793; 128/799; 128/898; 606/41; 604/20
[58] Field of Search ..................... 606/32, 34, 37–42, 606/45, 48–52; 128/783, 791, 793, 799, 898; 604/20

[56] References Cited

U.S. PATENT DOCUMENTS

| | | | |
|---|---|---|---|
| 2,249,894 | 7/1941 | Goldenstein | 606/50 |
| 4,326,529 | 4/1982 | Doss et al. | 606/34 |
| 4,564,016 | 1/1986 | Maurice et al. | 128/645 |
| 5,025,811 | 6/1991 | Dobrogowski et al. | 606/41 |

OTHER PUBLICATIONS

Berens et al. (1949) J. Trans. Am. Opthamol. Soc. 47:364–382.
Maurice (1983) Ocular Inflam. Ther. 1:97–102.
Fishman et al. (1984) Invest. Opthamol. Vis. Sci. 25:343–345.
Hughes et al. (1984) Arch. Opthalmol. 102:1825–1829.
Barza et al. (1986) Opthalmol. 93:133–139.
Maurice (1986) Opthalmol. 93:128–132.
Choi et al. (1988) J. Ocular Pharmacol. 4:153–164.
Grossman et al. (1989) Opthalmol. 96:724–729.

*Primary Examiner*—David M. Shay
*Attorney, Agent, or Firm*—Lahive & Cockfield

[57] ABSTRACT

Apparatus and non-invasive method for focal transcleral destruction of living human eye tissue. The apparatus includes a pair of conical-shaped probes, each probe filled with an ionic probe solution and having therein an electrode connected to a constant current supply. The method includes lowering the narrow aperture end of the probes onto the conjunctiva overlying the target tissue, each probe being approximately 90° apart from the other about the eye surface. The probes of the invention have opposite polarity to enable transfer of ions between the probes. Electrodes are of appropriate conductive materials.

7 Claims, 4 Drawing Sheets

ELECTROCYCLOABLATION APPARATUS AND METHOD

REFERENCE TO RELATED APPLICATION

The present application is a continuation-in-part of U.S. Pat. application Ser. No. 480,742, filed on Feb. 16, 1990, now U.S. Pat. No. 5,025,811, herein incorporated by reference.

BACKGROUND

This invention relates to an apparatus and non-invasive method for ablating eye tissue using transclerally delivered electric currents. A specific application of this invention includes reduction of intraocular pressure by focal destruction of the ciliary process.

Glaucoma is a potentially debilitating disease of the eye in which the intraocular pressure within the eye rises above normal levels. Glaucoma is generally treated by a surgical procedure where a small hole is introduced through the sclera, i.e., the outer coating of the eye, to allow fluid within the eye to drain into the subconjunctival space, between the conjunctiva and the sclera.

Cycloablation, i.e., destruction of the ciliary body, is another method by which an opthamologist can reduce intraocular pressure. The ciliary processes are involved in the production of fluid within the eye. Thus, by destroying the ciliary processes, aqueous production is reduced. Cylcoablation is primarily prescribed for advanced glaucoma patients with poor vision.

At present there are a number of cycloablative or cyclodestructive procedures. These procedures include cyclocryotherapy, transscleral Nd:YAG laser cycloablation, therapeutic ultrasound, cyclodiathermy, and transpupillary argon ciliary process photoablation. Potential side-effects associated with these procedures include a post-treatment pressure spike, marked intraocular inflammation and unpredictability. The degree of unpredictability is such that in some cases phthisis bulbi ensues. A preferred technique would be one which is more predictable, and associated with minimal inflammation.

Iontophoresis, i.e., a means of introducing drugs in ionized form into tissues by passage of electric current, has become increasingly popular in North America over the past several years. Its applications range from dye-enhance ablation with laser sclerotomies to the experimental treatment of keratitis and endophthalmitis using antibiotics. Most research concerning the use of iontophoresis utilizes the method as a non-invasive mode of introducing effective levels of drugs to various regions of the eye, such as the vitreous humor. Using existing methods of drug administration, current, probe diameter and time parameters are regulated to avoid tissue damage. See, for example, U.S. Pat. No. 4,564,016 to Maurice et al.

One reference, Berens, Sheppard, and Duel, *Cycloelectrolysis for Glaucoma*, J. Trans. Am. Opthalmol Soc. 47:364-382 (1949), describes the use of electricity to destroy the ciliary body. The technique described involves invasive insertion of a needle directly through the sclera into the ciliary body. In a majority of cases, dissection of the conjunctiva was required and 50-75 punctures were recommended. While such invasive means did alleviate ocular pressure, complications such as infections may arise related to the procedure and the procedure never gained acceptance because of its invasive nature.

Thus, there remains a need for a non-invasive means for relieving intraocular pressure and an efficient, less traumatic means for selectively ablating eye tissue.

SUMMARY OF THE INVENTION

The present invention features an apparatus and improved method for selectively ablating eye tissue, including a non-invasive method for reducing intraocular pressure by focal destruction of the ciliary body of a human eye using electric currents which are transclerally delivered by means of dual probe electrodes.

The apparatus of the present invention includes an adjustable direct current source (which may be a constant current supply or a voltage supply), and at least one probe assembly. The probe assembly includes a hollow probe and an electrically charged electrode suspended therein. The hollow probe further includes an aperture at a distal end to receive a conductive electrode. In one embodiment, the probe includes an aperture of predetermined diameter at the opposite, proximal end. The aperture of the distal end may be used to fill the probe with a selected salt solution having a predetermined ion concentration, e.g., by means of a syringe or mechanical pump.

The apparatus may include one probe assembly and a ground, or two probe assemblies. In the embodiment having two probe assemblies, one of the two probes includes a conductive material (e.g., metal) electrode which is electrically connected to the positive terminal of a constant current supply. This first probe is filled with a salt solution containing a predetermined concentration of a negative ion capable of electrochemically depositing onto the conductive material. For example, if the electrode is silver (Ag), the probe solution contains a predetermined concentration of chloride ions $(Cl-)$.

The second probe includes an electrode made of a metal/metal salt composition (i.e., Ag/AgCl) or material with similar characteristics which can transfer negative ions. The electrode is electrically connected to the negative terminal of a variable direct current supply. The probe is filled with a salt solution of a predetermined concentration of the negative ion of a salt of the electrode metal, at a concentration sufficient to enable transfer of the negative ions across the eye structure between the two probes without causing excessive damage to the surface of the eye, i.e., non-target eye tissue, during ion transfer.

In the embodiment having a single probe assembly and a ground, the probe electrode may be connected to either the positive or negative terminal of an adjustable direct current source. If the probe electrode is positive, then the electrode material is a substantially pure conductive material (e.g., metal), and the probe filling solution contains a predetermined concentration of a salt in which the negative ion is capable of electrochemically depositing onto the conductive material. The ground electrode may be a combination metal/metal salt electrode or similar materials.

Conversely, if the probe electrode is negative, the probe electrode material is a metal/metal salt combination or similar material. In that instance, the opposite electrode is made of a pure conductive material (e.g., metal), and is suspended in a salt solution.

In accordance with a method of the present invention, the two probes of a dual-probe ablation apparatus, as described above, are placed on the scleral surface of a human eye proximate to the target eye tissue to be ablated. The probes are placed spatially apart from one another by approximately 90 degrees. In a preferred form of practicing the method of the invention, the probes and current are substantially simultaneously applied to the scleral or conjunctival surface of the target eye. In addition, the probes may repeatedly be placed on the surface of the eye to be treated, and may remain on the surface for a predetermined amount of time.

It is an object of this invention to provide an ablation apparatus for effective, non-invasive ablation of selected eye tissue.

It is another object of this invention to provide an effective, well-controlled, minimally traumatic method for ablating eye tissue.

Other objects, features, and advantages of the invention will be apparent from the following description of the preferred embodiments thereof, and from the claims.

DESCRIPTION OF THE PREFERRED EMBODIMENT

The drawings will first briefly be described.

DRAWINGS

Like reference characters in the respective figures indicate corresponding parts.

Structure

Figure 1:
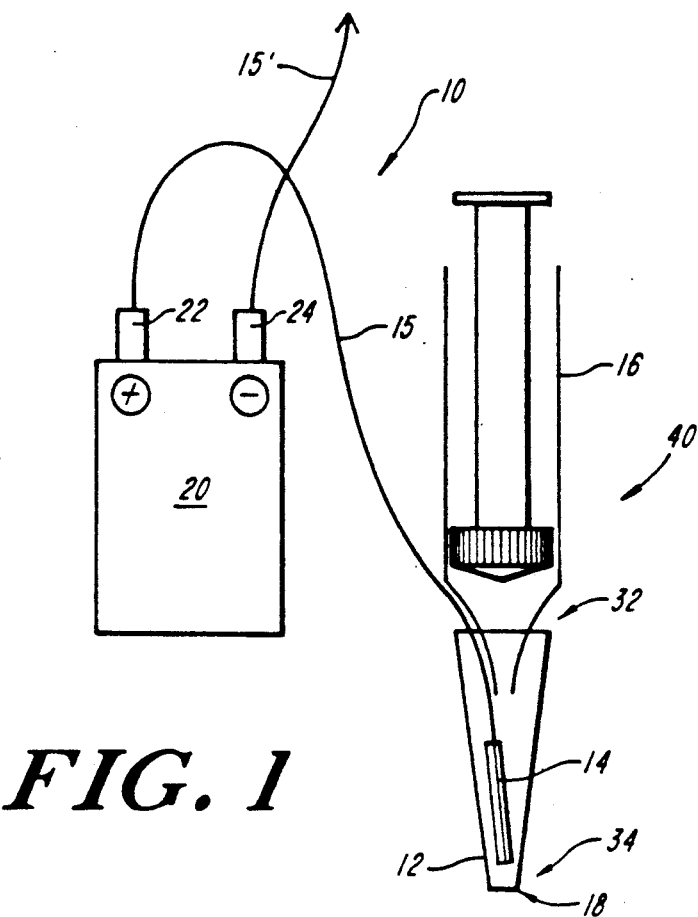
FIG. 1 is a diagrammatic representation of a single probe of the electroablation system of the present invention.

Referring to FIG. 1, an electroablation apparatus 10 includes an adjustable direct current source 20 having a positive terminal 22 and a negative terminal 24. The apparatus 10 further includes a probe assembly 40. The probe assembly 40 includes a probe 12, filled with a probe solution, and an electrode 14 connected to the current supply 20 via electrode lead 15. The electrode lead 15 enters the probe 12 through a top, distal end 32, terminating with an electrode 14. Ions are passed from the electrode 14 out of the probe 12 at proximal end 34. The proximal end 34 may include an aperture 18. The negative terminal 24 of the current supply 20 may be connected to another probe assembly via electrode lead 15' or ground.

Figure 4:
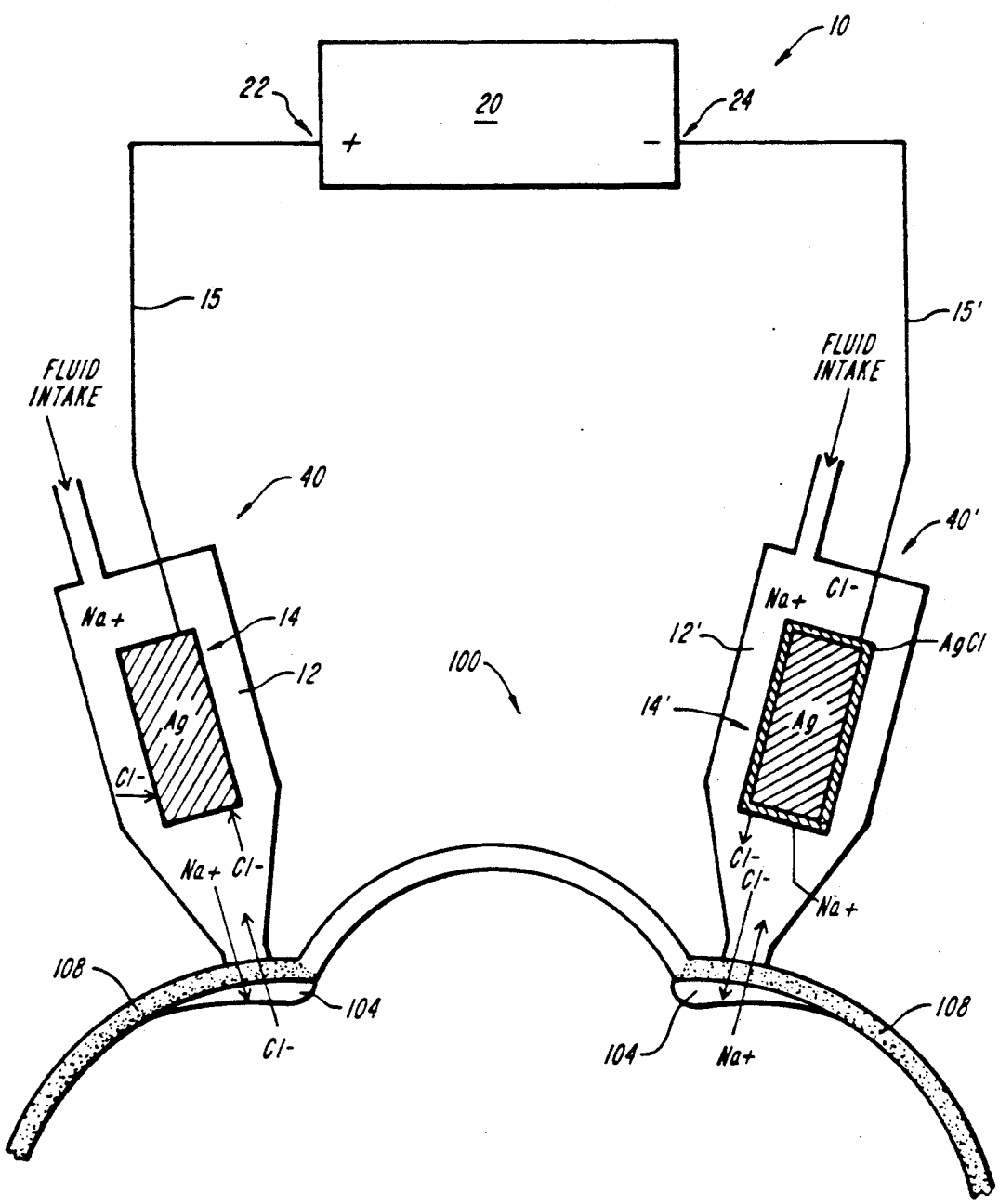
FIG. 4 is a schematic representation of a dual-probe ablation apparatus embodying the present invention as applied to an eye.

In an alternate embodiment of the assembly 10 of the invention, and as shown in FIG. 4, an electroablation apparatus 10 includes two probes 12, 12' each filled with a probe solution, and each having an electrode 14, 14', respectively, of the appropriate material connected to a variable direct current supply 20.

One aspect of the invention is that focal destruction of tissue sensitive to current or ion flow occurs in the region directly underlying the probes. The specific combination of both the probe electrode and the probe solution compositions achieve the requisite ion transfer, and are discussed in further detail below.

Figure 2:
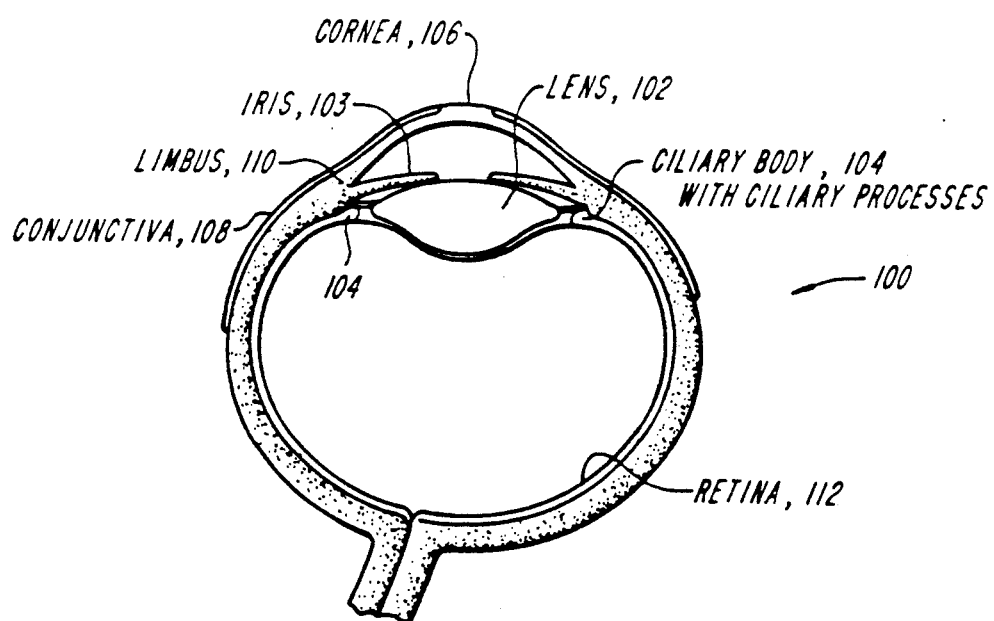
FIG. 2 is a schematic cross-sectional view of a human eye.

Referring now to FIGS. 2 and 4, use of the apparatus 10 involves repeatedly placing the two probes 12, 12' onto the conjunctiva 108 of a human eye 100 overlying the ciliary body 104 or other target eye tissue such that electrical current passes from the current supply 20 through the appropriate electrode to either the ground or to another electrode. This results in focal destruction of the ciliary body 104 or other sensitive target eye tissue underlying the probes 12,12'.

The following is a description of a single probe assembly 40 of the invention, however, the description applies equally to the other probe assembly 40' of the dual-probe embodiment of the invention. The probe 12 is generally conical-shaped and hollow, having one distal end 32 large enough to receive a filling means 16 for the probe solution. The other, proximal end 34 of the probe 12 may include an aperture 18 of predetermined diameter. The probe 12 is made of any non-conductive material, such as a plastic or glass, or insulated material. For example, the probe may be made from a glass Pasteur pipet which has been heated and pulled to have an appropriate aperture size. The probe may be reusable, or disposable and should be capable of being sterilized, e.g, autoclavable.

The electrode 14 may be manufactured from any conductive material, for example a pure metal or metal/metal salt composition. The exact electrode composition depends upon the ion to be transferred, the composition of the probe solution, and the polarity of the current source. Each electrode is within the distal end of a probe, and suspended in the appropriate filling solution. Each electrode is connected to the appropriate terminal of a variable direct current supply 20. The electrode 14 is suspended in the filling solution in the body of the probe 12 near the proximal end 34.

In the preferred embodiment of the invention, and as illustrated in FIG. 4, the ablation apparatus 10 consists of two probe assemblies 40, 40' having opposite polarity. The electrode lead 15 of one probe 12 is connected at one end to the positive terminal of a variable direct current supply 20 and at the other end to the electrode 14. This electrode 14 is preferably manufactured from a pure metal, e.g., silver (Ag) and is surrounded by a salt solution.

The other probe assembly 40' of the illustrated ablation apparatus 10 includes an electrode lead 15 which is connected at one end to the negative terminal of a variable direct current supply 20 and at the other end to the electrode 14'. This electrode 14' is manufactured from a metal/metal salt (e.g, Ag/AgCl), which permits transfer of negative ions to the surrounding probe solution.

Each probe 12, 12' is filled with the respective salt solutions by a filling device 16. This device 16 may be a syringe or tube, and is used to fill the probe with the selected probe solution. If a syringe is used, it may be attached to a flow pump, which delivers a constant flow of solution at a predetermined flow rate. Alternatively, a tube may be used, similarly attached to a pump having a predetermined flow rate.

Figure 5:
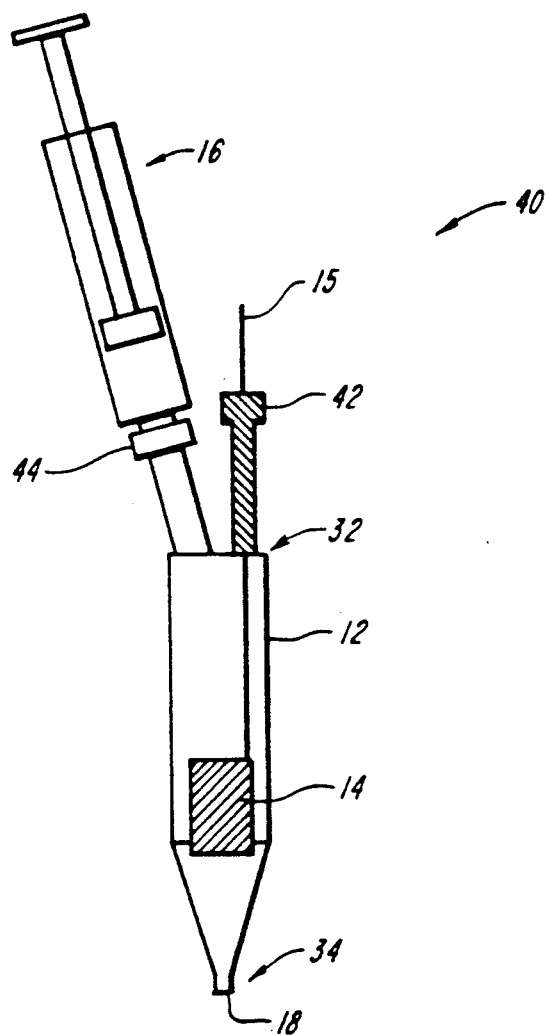
FIG. 5 is a diagrammatic representation of an alternate embodiment of the probe of the invention.

As illustrated in FIG. 5, the probe assembly 40 may include a probe 12, having an electrode 14 suspended therein. A sealable port 42 may be attached to the top distal end 32 of the probe 12 for introduction of the electrode lead 15 into the probe 12 without loss of probe filling solution. A connector 44 for connecting a filling device 16 may also be attached at the distal end 32 of the probe 12. In the illustrated embodiment, the filling device 16 is a syringe, and the connector 44 is a leuer lock type connector. Probe solution is thus introduced through the syringe 16 and flows out through aperture 18 at proximal end 34.

Figure 3:
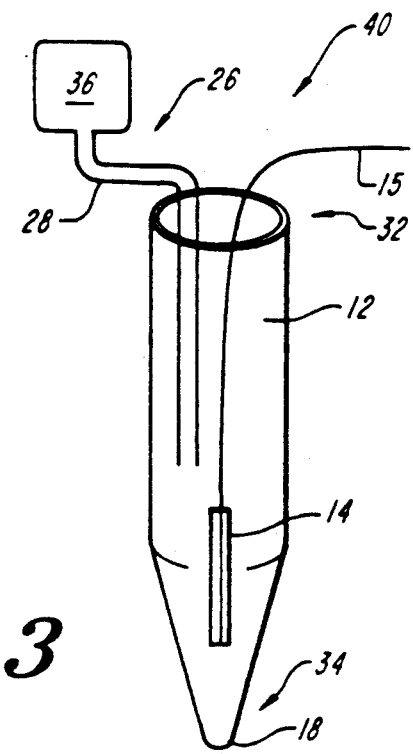
FIG. 3 is a diagrammatic representation of a single probe of the electroablation system of the invention having a filled glass pipet as a probe.

In one embodiment of the invention, as shown in FIG. 3, each probe may have a related perfusion system 26 for providing a constant flow of solution through the probe. Such a system 26 keeps fresh solution flowing into the probe 12 from perfusion pump 36 via a perfusion tube 28. Used solution may flow out of the probe 12 via a perfusion aperture 18. The constant flow assures replenishment of the ions in solution, and maintains the pH of the solution within the probe.

Figure 6:
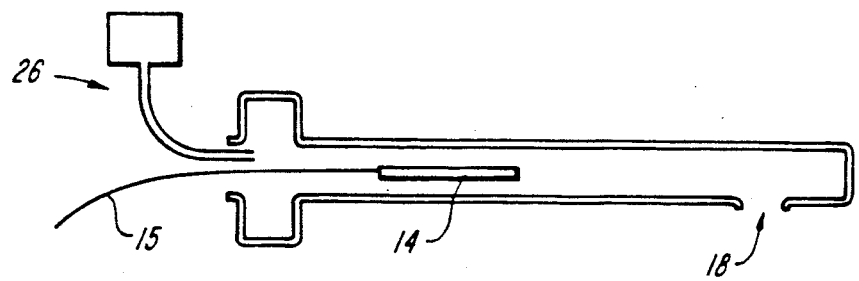
FIG. 6 is a diagrammatic representation of an alternate embodiment to the probe of the invention.

In yet another embodiment of the invention, as shown in FIG. 6, the aperture 18 is positioned on the side of the probe 12. A perfusion system 26 may be used, in a manner similar to that used for the illustrated embodiment of FIG. 3. In practicing the method of the present invention, the probe assembly 40 shown in FIG. 6 is used by positioning aperture 18 on the eye surface, as further described below.

One method for performing electrocycloablation is described in parent application U.S. Pat. application Ser. No. 480,742. In the present, dual probe system of the invention, a combination of a metal/metal salt electrode and a metal only electrode improves the effect of electrocycloablation. While a constant current is being delivered to the electrodes during electrocycloablation, the voltage across the system often significantly varies. In the present system, voltage can be stabilized to a given level by taking into account the following considerations:

(1) Use of specific metal or metal salt combinations for electrode materials;

(2) Appropriate concentration of NaCl within the probes.

The following presents the present understanding of the system of the invention, and is not intended to limit the inventive system.

Because the electrodes are in saline solutions, the following reactions occur:

Positive Electrode:

$$2Cl^- \longrightarrow Cl_2(g) + 2e^-$$

$$2H_2O \longrightarrow O_2(g) + 4H^+ + 4e^-$$

Negative Electrode:

$$Na^+ + e^- \longrightarrow Na$$

$$2Na + 2H_2O \longrightarrow 2NaOH + H_2(g)$$

$$2H_2O + 2e^- \longrightarrow H_2(g) + 2OH^-$$

These reactions result in gassing at both electrodes which increases the resistance in the system and results in failure to deliver current to the eye. To alleviate this problem, Ag and Ag/AgCl electrodes are used for the positive and negative probes, respectively. This allows the following reactions to occur at the electrodes:

Positive Electrode:

$$Ag(s) + Cl^- \longrightarrow AgCl(s) + 1e^-$$

Negative Electrode:

$$AgCl(s) + 1e^- \longrightarrow Ag(s) + Cl^-$$

As long as sufficient charge carriers are present in the solution and available on the surface of the electrode, significant voltage changes during the procedure may be avoided. For example, at a current of 5 mAmps the following voltages will be generated in probes with diameters of 500 μm and 1000 μm:

| Current Density (mAmp/cm²) | NaCl (wt % in water) | Voltage generated (volts) |
| --- | --- | --- |
| 2546 (500 μm diameter probe tip) | 1 | 59.7 |
| | 2 | 30.0 |
| | 6 | 14.5 |
| | 9 | 10.4 |
| | 13 | 8.0 |
| | 17 | 6.8 |
| | 19 | 5.8 |
| | 22 | 5.5 |
| | 25 | 5.1 |
| | 28 | 5.1 |
| 637 (1000 μm diameter probe tip) | 1 | 24.4 |
| | 2 | 15.8 |
| | 6 | 7.1 |
| | 9 | 5.1 |
| | 13 | 4.0 |
| | 17 | 2.9 |
| | 19 | 2.8 |

Assuming that the ocular tissue resistance remains constant, the probe voltage may be minimized by using a solution concentration of 22-25% or greater NaCl by weight in water in a probe with a 500 μm diameter tip, and a solution concentration of 17-19% or greater NaCl by weight in water in a probe with a 1000 μm diameter tip.

While the electrocycloablation system of the invention can be practiced at salt concentrations as low as 0.5% NaCl by weight in water, the solution concentration should optimally be at a level where the probe resistance is minimized. Thus, smaller probe diameters will result in a higher current density and higher voltages than a larger probe given the same current, and may require a higher salt concentration to minimize probe voltage or resistance.

Method

FIG. 2 is a cross-sectional view of a human eye 100 showing the relative location of the iris 103, ciliary body 104, conjunctiva 108, cornea 106, retina 112, and lens 102. The method of the present invention involves non-invasive focal destruction of the ciliary body 104 with its processes, and/or the retina 112.

The method of the invention involves lowering the proximal end of probes 12, 12' onto a patient's eye 100, as shown in FIG. 4. The probes are lowered into position by mechanical or manual means. A stereotaxic harness may be used to allow accurate placement of the probes 12, 12' on a desired location of the eye. Mechanical devices which allow for horizontal, vertical, and z-axis movement of the probes 12, 12' are preferred. Alternatively, the probes may be hand-held, and touched on the eye using visual aids such as a head-mount monocular or binocular scope. It is also possible to have a computer-controlled system which would move each probe separately, or in a coordinated pattern about the eye.

For electrocycloablation of a ciliary body 104, one probe 12 is placed posterior to the edge of a cornea 106 overlying a selected region of the ciliary body 104, as shown in FIG. 4. The second probe 12' of the invention is placed posterior to the edge of the same cornea 106 overlying another region of the ciliary body 104. Positioning of the probes relative to each other is described further below.

The parameters suitable for use in conjunction with the above-described electroablation system are selected to minimize inflammatory response and to maximize the amount and duration of intraocular pressure reduction.

EXEMPLIFICATION

There follows an example of use of the dual-probe electroablation system embodying the present invention as used for intraocular pressure reduction. This example is not limiting to the invention. In this example, parameters were chosen to achieve a 40% pressure reduction.

Prior to treatment with the apparatus of the invention 10, the eye is treated with a local retrobulbar anesthesia of 2% xylocaine/0.75% marcaine solution. A lid speculum is inserted between the eyelid and eye to be treated, to expose the eyeball, specifically the conjunctival surface. The eye may be irrigated with a balanced saline solution to keep the tissues moist.

To perform the ablation, one probe electrode is attached to the positive terminal of a constant current supply, and the other probe electrode is attached to the negative terminal of a constant power supply. The electrode and probe solution are made in accordance with the description and parameters described above. The current may either be turned on prior to or following placement of both probes. The probes are then placed on the conjunctiva 108 overlying the region of the ciliary body 104 or retina 112 to be ablated.

For cycloablation, the probe is placed approximately 2 millimeters from the limbus 110. Each probe is visually placed spatially apart from one another by approximately 90° or using an assembly which fixes the distance between the probes. A caliper can be used to measure distances.

The current is turned on via a foot switch and gradually increased to 5.0 milliamps. The range is preferably between 1.5 to 8.0 milliamps. The exact amperage per treatment depends on the specific structure to be ablated and/or the nature of damage desired. For cycloablation, this current is then maintained at each location for both probes for 30 seconds to 5 minutes. The exact time may be maintained by an automatic timer. The process is repeated approximately 5–15 times, or a total of 10–30 spots, around the circumference of the eye, exclusive of the 3 o'clock and 9 o'clock positions. By slowly increasing the current from zero to the desired level, patient discomfort may be minimized.

Following application of the probes, the eye is irrigated with saline solution. A topical application of a 1% atropine/1% prednisilone acetate plus antibiotic solution is post-operatively applied to the eye. A subconjuntival steroid may also be applied. A patch is used to cover the eye during post-operative recovery.

Other embodiments are considered to fall within the scope of the following claims.

What is claimed is:

1. A non-invasive method for focal non-invasive transcleral destruction of living human eye tissue, comprising the steps of:
    A. providing a constant current supply having a positive terminal and a negative terminal;
    B. providing a pair of hollow probes, each of said probes having a distal end and a proximal end, and a first aperture at said distal end of each hollow probe to receive a conductive electrode of predetermined composition and means for filling said probe with a predetermined solution;
    C. connecting said conductive electrode of one of said probes to said positive terminal, defining a first probe, and connecting said conductive electrode of the other of said probes to said negative terminal, defining a second probe;
    D. filling each of said probes with a solution of predetermined ionic concentration;
    E. adjusting said constant current supply to a predetermined current;
    placing, substantially simultaneously, said proximal ends of said probes repeatedly onto a surface of a human eye proximate to target eye tissue at a plurality of locations; and
    G. maintaining movement of said proximal ends for a predetermined duration.

2. The method of claim 1 wherein said placing includes positioning said proximal ends spatially apart from one another, by approximately 90 degrees.

3. The method of claim 1 wherein said conductive electrode of said first probe comprises a substantially pure metal, and wherein step D further comprises filling said first probe with a probe solution having a concentration of said negative ion of a salt of said electrode metal in an amount sufficient to transfer ions into said target tissue and prevent excessive damage to said surface of said human eye.

4. The method of claim 3 wherein said conductive electrode of said second probe comprises a metal/metal salt composition, and wherein step D further comprises filling said second probe with an ionic probe solution having a concentration of a negative ion of a salt of said electrode metal.

5. The method of claim 1 wherein said placement step F is repeatedly performed for a predetermined number of times.

6. The method of claim 1 wherein placement step F is performed prior to adjusting step E.

7. The method of claim 1 further comprising the step of substantially simultaneously rotating each of said probes about said target eye tissue.

* * * * *